United States Patent [19]

Walker

[11] Patent Number: 5,420,961
[45] Date of Patent: May 30, 1995

[54] STEAMING DEVICE

[76] Inventor: Cedric T. M. Walker, 1900 S. Eads St., Apt. 933, Arlington, Va. 22202

[21] Appl. No.: 187,722

[22] Filed: Jan. 28, 1994

[51] Int. Cl.⁶ .............................................. F22B 1/28
[52] U.S. Cl. .................................... 392/404; 392/403
[58] Field of Search ............... 392/403, 404, 402, 401; 422/305, 306, 125; 239/240, 241, 587.5, 587.6

[56] References Cited

U.S. PATENT DOCUMENTS

| | | | |
|---|---|---|---|
| 1,421,756 | 7/1922 | Arnao . | |
| 1,930,038 | 10/1933 | Crowley et al. . | |
| 2,184,679 | 12/1939 | Myrick | 392/403 |
| 2,272,585 | 2/1942 | Rocke | 239/587.5 |
| 2,345,813 | 4/1944 | Harriman | 239/587.6 |
| 2,467,393 | 4/1949 | Leher | 392/401 |
| 2,561,443 | 7/1951 | March | 392/404 |
| 2,810,167 | 10/1957 | Parks | 422/125 |
| 3,152,240 | 10/1964 | Scott . | |
| 3,472,455 | 10/1969 | Johnson | 392/403 |
| 3,581,529 | 6/1971 | Mitchell | 392/403 |
| 3,749,092 | 7/1973 | Williams . | |
| 4,277,029 | 7/1981 | Rabitsch | 239/240 |
| 4,292,971 | 10/1981 | Smit et al. . | |
| 4,399,349 | 8/1983 | Deming et al. . | |
| 4,695,434 | 9/1987 | Spector | 422/125 |
| 4,810,854 | 3/1989 | Jursich | 392/405 |
| 5,098,414 | 3/1994 | Walker | 604/291 |
| 5,278,937 | 1/1994 | Alix | 392/402 |

Primary Examiner—Teresa J. Walberg

[57] ABSTRACT

A steaming device includes a reservoir for containing a predetermined quantity of water, a heater for heating the water and producing the steam, a nozzle for exhausting out the steam, a conduit for connecting the nozzle with the reservoir, and an external support structure for supporting components of steaming device. The nozzle make up part of a programmable automatic flow adjusting system for selectively varying the direction and speed of the steam flowing out therefrom.

18 Claims, 3 Drawing Sheets

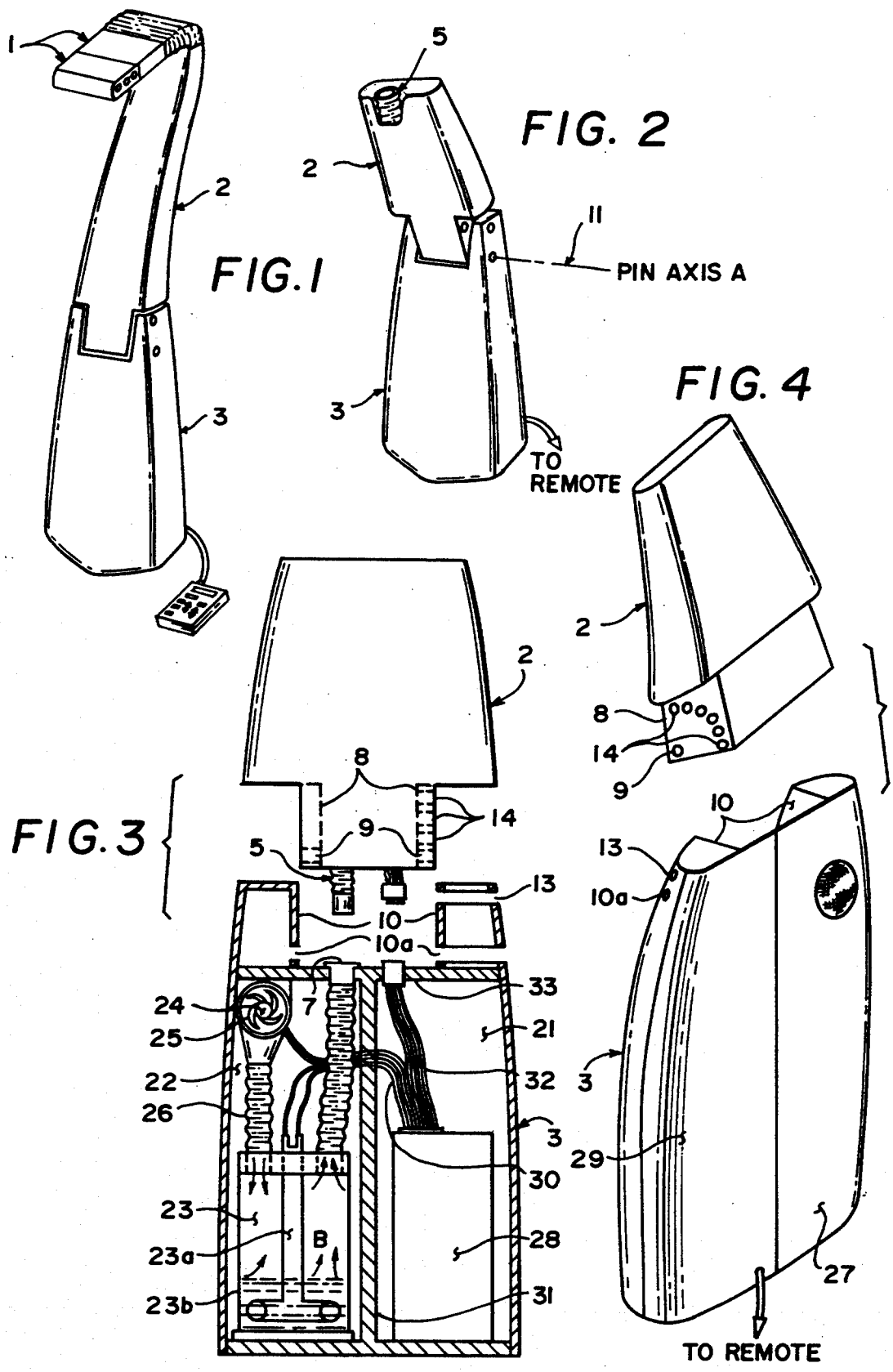

STEAMING DEVICE

FIELD AND HISTORICAL BACKGROUND OF THE INVENTION

The present invention is directed to a steaming device, and more particularly to a cosmetic skin treatment device for applying heat in the form of steam to an area of human skin and is an improvement of my prior U.S. PAT. No. 5,098,414.

The human skin has been known to develop various disorders that most persons suffer from, especially during their teenage years, such as "acne". This disorder develops due to endocrine activity of certain glands in the body during the adolescence. Among others, this endocrine gland activity affects the sebaceous glands of the skin. Due to this activity, an oily substance, known as "sebum" tends to collect and clog pores in the skin thereby producing the acne disorder. The acne tends to blemish the skin which, from an appearance, as well as the psychological point of view, is undesirable. One way to eliminate or substantially reduce the effects of acne has been to periodically cleanse the skin by first applying heat to the skin for thereby opening the pores, and then removing the oily substance therefrom.

Various skin treatment devices have been proposed, and a few examples are shown in U.S. Pat. Nos. 1,421,756; 1,930,038; 3,152,240; 3,749,092; 4,292,971; and 4,399,349. The conventional devices, however, suffer from the disadvantage that they produce an intense non temperature controlled flow of steam which is continuously directed to a specific portion of the skin. Due to this arrangement, the skin is prone to scalding or scorching. In addition, only a relatively small area of skin can be subjected to steaming or heating at one time, due to the fact that in conventional systems the user has to manipulate the steam exhaust nozzle in order to heat or steam, for example, another area of the skin. Therefore, there is a need in the art for a steaming device which does not suffer from the disadvantages noted above.

SUMMARY OF THE INVENTION

The principal object of the present invention is to provide a steaming device for use in connection with steaming or heating human skin that does not suffer the disadvantages associated with conventional devices.

An object of the present invention is to provide a steaming device which can be used to steam or heat an area of human skin.

Another object of the present invention is to provide a steaming device which is simple in construction, easy to use and relatively inexpensive to manufacture.

Yet another object of the present invention is to provide a steaming device which is versatile in that it can be used to steam or heat a smaller skin area as well as to heat or steam a relatively large area of the skin.

An additional object of the present invention is to provide a steaming device which will apply steam or heat at an elevation above floor surface that is conducive to safe and comfortable steam applications to an area of human skin.

Still an additional object of present invention is to provide a steaming device which will apply steam in an optimized cubic zone relative to the floor, device, and human skin.

Still yet an additional object of present invention is to provide a steaming device that provides an external support structure to support the working components of the steaming device.

A further object of the present invention is to provide a steaming device that uses a hand-held computer control system to apply customized steam and heat to an area of human skin.

Still a further object of the present invention is to provide a steaming device that has the ability to perform a analysis of the skin and to modify steam conditions for that specific skin type.

Still yet a further object of the present invention is to provide a steaming device which can monitor and control the temperature of the steam.

A further object of the present invention is to provide a steaming device which can monitor and control the humidity of the steam.

Still a further object of the present invention is to provide a steaming device which can isolate herbs and oils from steam application and upon command mix herbs and oils with steam.

Yet further an object of the present invention is to provide a steaming device which is modular in design so as to be easily and quickly disassembled to a compact size for shipment purposes, and easily assembled in a relatively short time for use.

Another object of the present invention is to provide a steaming device which can be easily converted from a floor supported device to a table top appliance, and vice-versa.

Still another object of the present invention is to provide a steaming device which can be easily converted to a steam massaging device.

Still yet another object of present invention is to provide a steaming device which is lightweight and portable.

An additional object of the present invention is to provide a steaming device which can be used as a room humidifier.

In summary, the main object of the present invention is to provide a steaming device which is versatile, easy to manufacture and safe to use.

BRIEF DESCRIPTION OF THE DRAWINGS

The above and the other objects and advantages and novel features of the present invention will become apparent from the following detailed description of the preferred embodiment of the invention illustrated in the accompanied drawings, wherein:

FIG. 1 is a perspective elevational view of the steaming device of the present invention;

FIG. 2 is a partial perspective elevational view of the device shown in FIG. 1;

FIG. 3 is an enlarged partial longitudinal sectional view of the lower section of the device shown in FIG. 1;

FIG. 4 is a perspective elevational enlarged rear view of the lower section of device shown in FIG. 1;

DESCRIPTION OF THE PREFERRED EMBODIMENTS

Figure 5:
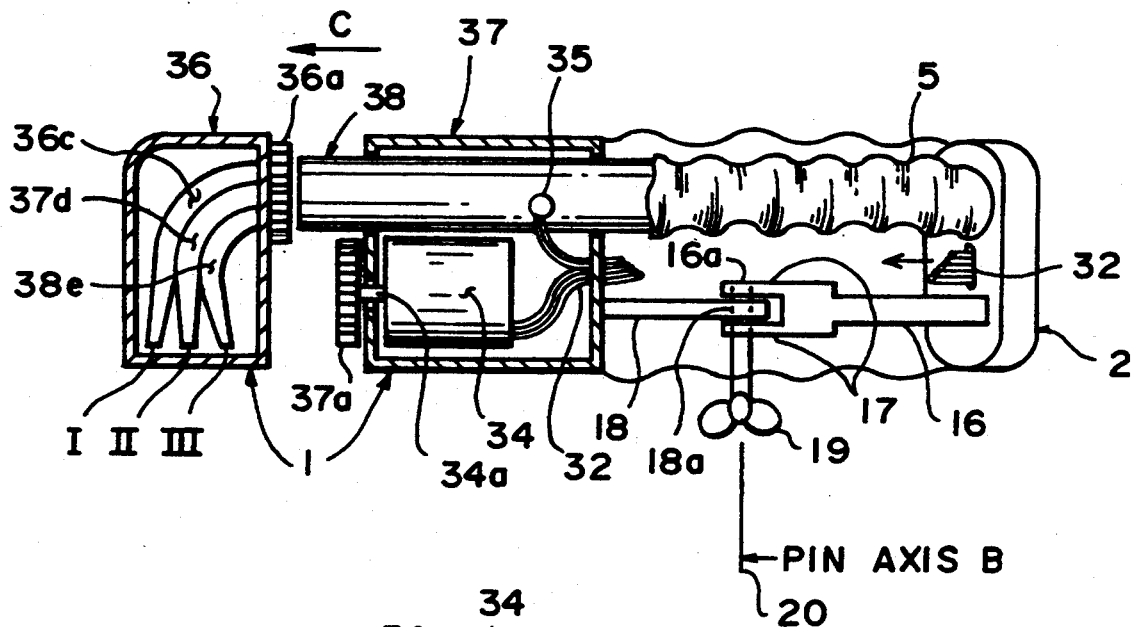
FIG. 5 is an enlarged partial longitudinal top sectional view of the nozzle section of the device shown in FIG. 1.

As best shown in FIG. 1, the steaming device A of the present invention is comprised of a two (2) piece nozzle section 1 designated Part One and Part Two, upper external support structural section 2 and lower external support structural section 3. The steaming device preferably has a total height of approximately four (4) feet and is constructed as to be supported by the floor. It should be understood, however, that the steaming device A of the present invention can be constructed so as to be a table top model.

As best shown in FIG. 2, upper external support structure 2 is elliptical in configuration and is rigid in make up and serves as an upper external support structure and protection for a steam conduit 5 made of a rubber like or other suitable material. The conduit 5 includes a watertight seal connection at its upper and lower ends and is shown in FIG. 3 for the lower end as being connectable by use of a releasable mounting 7 to the lower external support structural section 3.

As shown in FIGS. 3 and 4, each of the side panels 8 of the upper external support structure 2 includes holes on both sides at its lower end at the forward portion 9. These holes 9 accommodate a rod which when the side panels 8 of the upper external support structure 2 are positioned so as to align holes 9 of side panels with corresponding holes 10a in side panels 10 of the lower external support structure 3, allows the upper external support structure 2 to pivot about a pin axis (width-wise rotation) at 20.5 inches above floor level ±10 inches and defined therein Pin Axis A 11 as best seen in FIG. 2. As best shown in FIG. 2, the steaming device has a lock mechanism which allows the upper external support structure 2 to be held in chosen positions as the upper external support structure pivots about the Pin Axis 11. This arrangement allows the two (2) piece nozzle section 1 to be adjusted to various heights above floor and various distances forward of lower external structure 3.

Steam treatments can be applied to the body in many different positions. The three most common are: 1) sitting erect in a chair, 2) reclined in a chair, and 3) lying down, whether on a bed or couch, etc. Each position has its preferred zone (cubic space), relative to an area of skin and the floor, in which a steam being exhausted from a steaming device gives the most beneficial treatment. In the sitting erect position, a nominal chair's seating surface is about 18 inches above the floor. The chest and facial area of an average size person sitting in a nominal chair is about 36 to 48 inches above the floor and the centerline of the body is about 7 to 15 inches from the side or edge of the chair (i.e., center of treatment zone is acting along the centerline axis of the chair and body). This treatment zone is forward of face and chest area. This description holds true for the reclined position as well except for the chest and facial area of an average person is 24 to 36 inches above the floor. In the lying down position, a nominal bed or couch is about 13 to 24 inches above the floor. The chest and facial area of an average size person lying on a bed or couch is about 19 to 33 inches above the floor and about 7 to 15 inches (centerline of body) from the edge of the bed, couch, etc. The treatment zone in this application should be above the centerline of the body. Looking at all three of these applications for commonality, yields an optimized treatment zone (cubic space) for all three applications.

The base of the optimize treatment zone starts at 19 inches above the floor surface and has the dimensions of 40 length (extends from head to toe) by 29 height by 20 width (extends the width of body) inches or 23,200 cubic inches. The optimized treatment zone, is defined as a rectangular box suspended in space by which, if an area of skin is treated, whether the body is sitting erect, sitting reclined, or lying down on a bed or couch, within this defined rectangular box will receive an optimized treatment. Pin Axis 11 of the device is optimized (i.e., height above floor) such that it allows the upper external support structure 2 to position nozzle section 1 to a desired position within the defined optimized treatment zone while clearing the edges of chairs, beds, etc.

As best seen in FIGS. 3 and 4, the lock mechanism is comprised of three parts, 1) side panel 8 of the upper external support structure 2, 2) the side panel 10 of the lower external support structure 3, and 3) a spring loaded locking rod (not shown). Located on the side panel 10 of the lower external support structure 3 is a hole and therein defined locking hole 13. Located on side panel 8 of the upper external support structure 2, at equal distance from Pin Axis 11, in a semi-circle arrangement are holes and therein defined adjustment holes 14. When the upper external support structure 2 is allowed to pivot about Pin Axis 11 (as best seen in FIG. 2), one of the adjustment holes 14 will align with the locking hole 13. When the spring loaded locking rod is positioned through the locking hole 13 and one of the adjustment holes 14, the upper external support structure 2 is held in a desired position.

Figure 6:
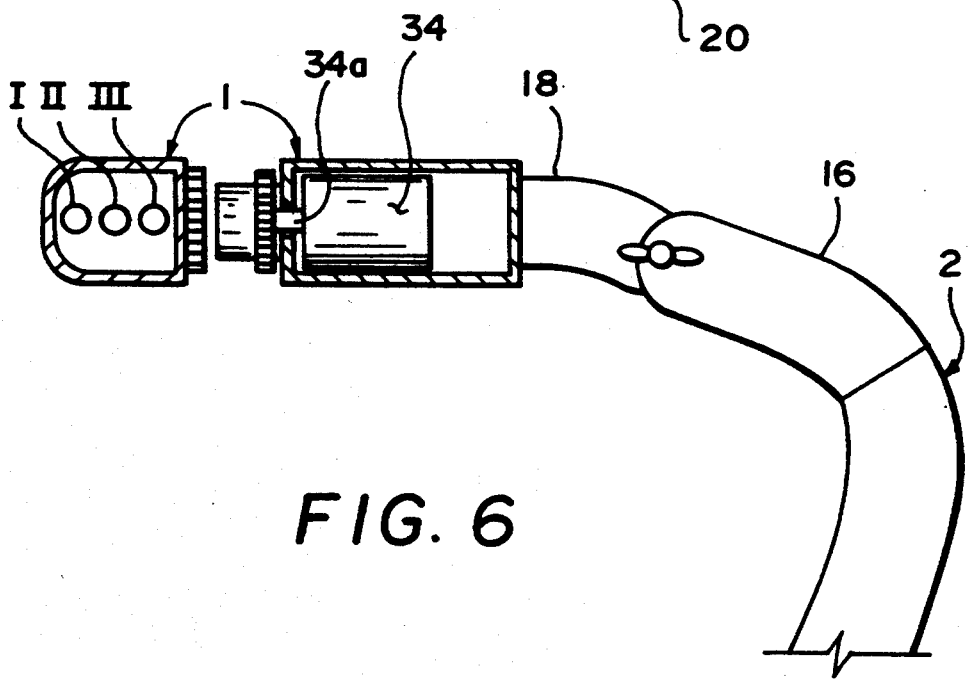
FIG. 6 is an enlarged partial longitudinal side view of the nozzle section of the device shown in FIG. 1.

As shown in FIGS. 5 and 6, the upper end of the upper external support structure section 2 includes a protruding one quarter shaped piece 16 and define therein lower quarter piece 16. The lower quarter piece 16 has two side plates on its end 17 for snugly receiving a slightly thinner almost identical one quarter shaped piece 18 protruding from nozzle section 1 therein defined upper quarter piece. The upper quarter piece 18 and the lower quarter piece 16 communicates via holes 18a and 16a, respectively. Holes 16a and 18a when aligned accommodate a butterfly screw 19 as best seen in FIG. 5. The butterfly screw 19 allows the nozzle section 1 to be suspended in a chosen position by tighten the butterfly screw which applies pressure to the upper quarter piece 18 of the nozzle section 1 by tightening the side plates 17 of the lower quarter piece 16 of the upper external support structure 2 against the upper quarter piece 18 of the nozzle section 1. By loosen the butterfly screw 19 the pressure against the upper quarter piece 18 of the nozzle section 1, is relieved, thus allowing the nozzle section 1 to rotate about a pin axis and defined therein Pin Axis 20. This allows nozzle section 1 to be adjusted to a level orientation relative to the floor when the upper external support structure 2 is rotated about Pin Axis A 11.

As best shown in FIG. 3 the lower external support structure section 3 is comprised of a right and left chamber 21 and 22, respectively. The left chamber 22 houses a water heater 23a and a container for containing water 23b and define therein reservoir or mixing chamber 23. When water in container 23b is heated, the water is converted into steam, shown by arrows B in FIG. 3. The steam flows through conduit 5 to be ultimately exhausted out through nozzle section 1. Also housed in left chamber is a suction motor 24 for driving fan 25 which draws exterior air into the reservoir 23 via conduit 26. The reservoir or mixing chamber 23 is accessible for re-filling and cleaning via a rear access panel door 27 mounted therein by conventional hinges and secured by a safety latch (not shown) as best seen in FIG. 4. The purpose of the right chamber 21 is to accommodate the water tight black box electronics 28. The right chamber 21 is accessible from the rear via an access panel 29 and secured by non-standard safety screws (not shown) best seen in FIG. 4. The access panel 29, when opened, provides easy access to chamber 21 for servicing water tight black box electronics 28. The black box electronics 28 are connected to water heater 23a and suction motor 24, via electrical wiring 30 channeled through vertical wall 31 which divides the left and right chambers. As best seen in FIG. 3, communication between black box electronics 28 and nozzle section 1 occurs through wiring 32 channeled through upper surface 33 of left chamber 21, which subsequently, traveling through the upper external support structure 2 and into nozzle section 1. As best seen in FIG. 1 the purpose of wiring 32 is to supply power to nozzle section 1 and to send and receive signals to and from the nozzle motor 34 and nozzle temperature sensor 35. An electric cable, to be connected to power source (not shown), supplies power to the water tight black box electronics. Some of this power is channeled to the hand-held remote control which then distributes the power and component commands via computer program to the heating element 23a, fan motor 24, and the nozzle section 1.

Figure 7:
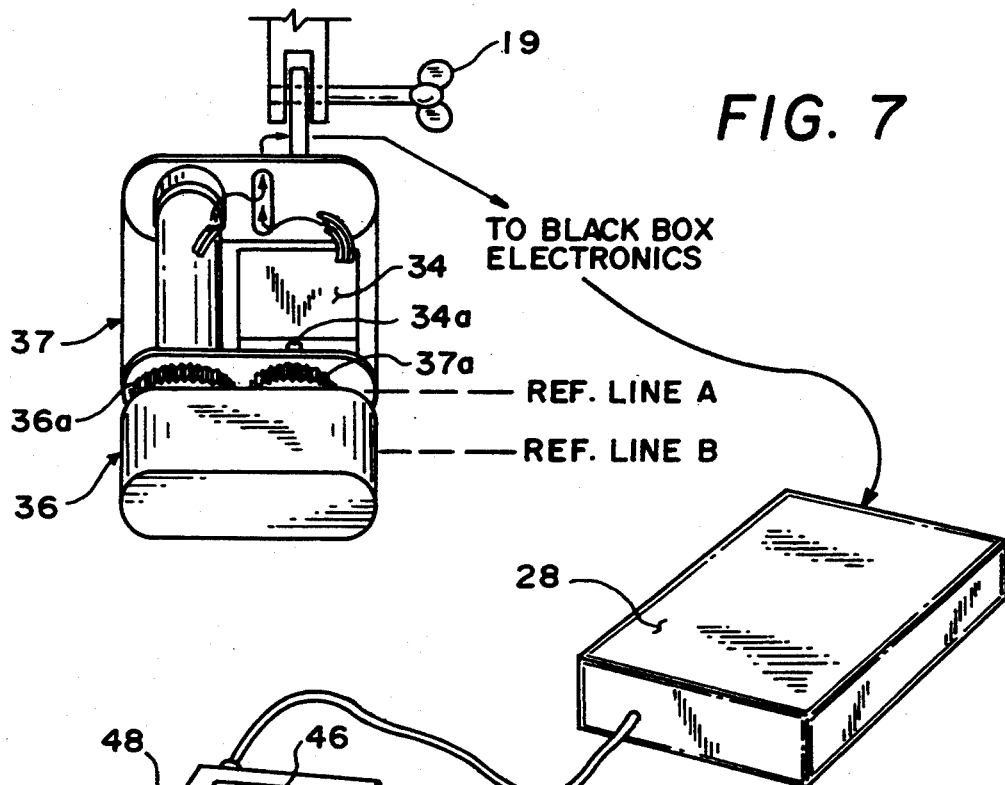
FIG. 7 is a perspective elevational enlarged view of the nozzle section of device shown in FIG. 1, with black box electronics, and hand-held remote control.
Figure 8:
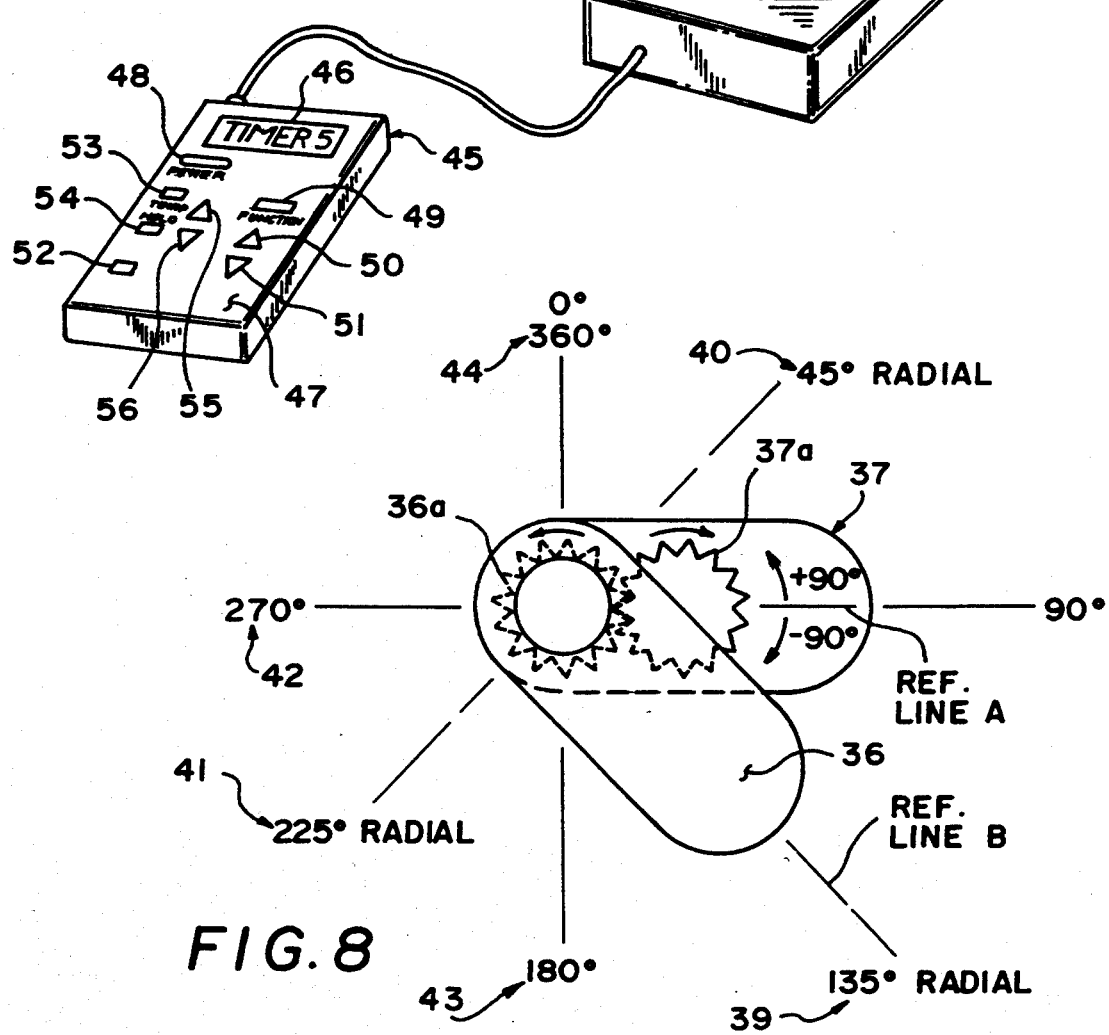
FIG. 8 is an enlarged front elevational view of the nozzle section shown in FIG. 5.

As best shown in FIGS. 5 and 6, the two (2) piece nozzle section 1 which consists of Part One 36 and Part Two 37 has an open communication with the exterior. Part One 36 communicates with Part Two 37 via a rigid tubular conduit 38 which protrudes from nozzle section Part Two 37 and two (2) sprockets 36a and 37a. The definition of Part One 36 encompasses a sprocket 36a which will be defined therein as Sprocket One. Sprocket One 36a makes the connection with Nozzle section Part One at the outside of the inside wall as best shown in FIG. 5. The definition of Part Two includes a sprocket 37a which is connected directly to the motor shaft 34a of Part Two of Nozzle section and will be defined therein as Sprocket Two. As best seen in FIG. 7 when Sprocket One 36a of Nozzle Section Part One 36 and Sprocket Two 37a of Nozzle Section Part Two 37 are combined in a locked fashion, Part One 36 of Nozzle Section 1 and Part Two 37 of Nozzle Section 1 are engaged. When Part One and Part Two of Nozzle section are engaged, this arrangement is defined therein as the Flow Adjusting Mechanism. When the shaft 34a of the control motor 34 rotates, Sprocket Two is caused to rotate. When Sprocket Two 37a moves in a clockwise direction, Sprocket One 36a moves in a counterclockwise direction, thus moving Part One as best shown in FIG. 8. The control motor 34 of the Part Two 37 of nozzle section 1 has a rotation range of 180 degrees which restricts Sprocket Two of Part Two of Nozzle Section 1 to a range of 180 degrees. It should be noted that the half range of the control motor 34 of Part Two of Nozzle section 1 is 90 degrees and acts along a reference line that extends through the horizontal plane and is labeled Reference Line A as best shown in FIGS. 7 and 8 and is therein defined as the neutral position. This means that Sprocket Two 37a of Part Two 37 of Nozzle Section 1 when at the neutral position can rotate 90 degrees clockwise from the neutral position and or 90 degrees counter clockwise from the neutral position.

As best shown in FIGS. 7 and 8, Part One 36 of Nozzle section 1 which includes Sprocket One 36a has a reference line that acts along the centerline of Part One 36 of Nozzle section 1 and when engaged with Part Two 37 of Nozzle section 1 projects a Reference Line along a particular radial and is labeled and defined therein Reference Line B. This arrangement allows Part One 36 which relates directly to Sprocket One 36a of Nozzle Section 1 to exhaust steam into the atmosphere ±90 degrees relative to Reference Line B. When Sprocket One 36a of Part One 36 is engaged to Sprocket Two 37a of Part Two 37 (Sprocket Two 37a is at it's neutral position and Sprocket Two 37a of Part Two 37 pivots ±90 degrees about the neutral position or Reference Line A), Sprocket One 36a of Part One 36 rotates ±90 degrees about Reference Line B. As best shown in FIG. 8, for example, if Sprocket Two 37a of Part Two 37 is at its neutral position and is engaged by Sprocket One 36a of Part One 36 with Reference Line B acting along a radial of 135 degrees 39, using the 360 degree compass system, will allow Part One 36 of Nozzle Section 1 to act ±90 degrees about the 135 degree radial 39 (i.e., rotate from 45 degree 40 to 225 degree 41). If reference line B is acting about the 270 degree radial 42, then Part One 36 of Nozzle section 1 can exhaust steam into the atmosphere from 180 degree 43 to 360 degrees 44 (i.e., ±90 degrees about the 270 degree radial 42).

As best seen in FIG. 5 Part One 36 of nozzle section 1 can be reconfigured to change the radial in which Reference Line S acts. This is accomplished by disengaging Sprocket One 36a of Part One 36 of Nozzle section 1 from Sprocket Two 37a of Part Two 37 of Nozzle section 1. Disengagement is executed by moving Part One 36 of nozzle section 1 outward along protruding rigid tubular conduit 38 of Part Two 37 of nozzle section 1 shown by arrow C. Part One 36 of nozzle section 1 is then free to rotate about protruding tubular conduit 38. Reference Line B of Part One 36 of Nozzle section 1 can then be given a new position by rotating Part One 36 of Nozzle section 1 about tubular conduit 38 and re-engaging Sprocket One 36a of Part One 36 of nozzle section 1 and Sprocket Two 37a of Part Two 37 of Nozzle section 1.

Part One 36 of Nozzle section 1 communicates with the exterior by exhausting an elliptical steam pattern into the atmosphere. To achieve an elliptical steam pattern, a nozzle communicating with the exterior would have divergent nozzle design which also because of the divergence causes the exit velocity and exit force to decrease. As best shown in FIG. 5, Part One 36 of Nozzle section 1 includes an internal design that does not suffer from this disadvantage. As best shown in FIGS. 5 and 6, Part One 36 of Nozzle section 1 includes three (3) internally mounted multi-directional converging nozzles I, II, and III which act along different radials. This nozzle arrangement forces Part One 36 of Nozzle section 1 to communicate with the exterior by exhausting steam in an elliptical pattern (relative to the centerline of nozzle II). Nozzle I and Nozzle III radials the centerline of Nozzle II anywhere from one (1) to forty-five (45) degrees. Each nozzle has a convergence angle which increases the velocity of the flow. As steam travels from Part Two 37 of Nozzle section 1 to Part One 36 of Nozzle section 1, steam is channeled into three (3) internal flow straightening channels 36c, 36d, and 36e before entering and the respective Nozzles I, II, and III. The Internal Flow Straightening Channels have a turn radii ranging from 3/16 of an inch to 2.5 inches. This design helps to reduce the introduction of turbulence into the flow due to the 90 degree turn in Part One 36 of Nozzle section 1.

As best shown in FIG. 7, various automated controls are provided in a small rectangular box 45 with nine (9) keypads and a liquid crystal display (LCD) or generic display 46 to form a a hand held remote control 47. When a keypad is depress on the Hand-Held Remote 47, the CPU or Central Processing Unit located internal to the remote control executes the command software located within the CPU which sends instructional commands to the components of the steam generator via the electronics 28. The electronics 28 are defined therein as a group of integrated circuits housed in a water-tight box which converts instructional commands from software to recognizable signals for components (i.e., heater 23a, fan motor 24, control motor 34, temperature sensor 35, etc.) and convert signals from components to recognizable data for processing by control software via the CPU. Each keypad has a specific use; ON/OFF keypad 48 toggles power to all systems, the function keypad 49 pulls down a menu of five functions (i.e., timer, heat, fan, nozzle angle, and nozzle speed) and by repeative depression of the function keypad gives the ability to move between functions, the up scroll keypad 50 and the down scroll keypad 51 allow movement within functions. For example, if the function keypad is depressed, the timer function will be displayed on the LCD 46 as best seen in FIG. 7. The up and down keypads 50 and 51, respectively, are then used to make adjustments to the timer function. If the up keypad 50 is depressed "Timer 0" goes to "Timer 5", meaning 5 minutes depressed up keypad 50 is depressed again "Timer 5" goes to "Timer 10" and so on, not to exceed "Timer 30". If timer function is at "Timer 10" and the down keypad 51 is depressed, "Timer 10" goes to "Timer 5" and so on with "Timer 0" being the minimum. If the function keypad 49 is depressed, the timer function is now set and the next function is now displayed on the LCD 46, in this case, the heat function, and so on. The info keypad 52, provides addition information to user during operation such as time, temperature, humidity, etc.

The temperature hold key 53, which when depressed activates the temperature hold command which maintains constant temperature during operation by commanding adjustments to the heater 23a and fan motor 24 to maintain a constant temperature. For example, if the dynamics of the steam generator changes such that the temperature increases above what is desired, then the temperature hold function via the electronics 28 and software will command the fan motor 24 to increase in speed, thus adding more external air to the system, thus decreasing the overall temperature or commanding a decrease in heater 23a setting, so as to bring temperature back to the commanded temperature. If adjustments to the commanded temperature are desired, the up keypad 55 can be depressed to increased the commanded temperature or the down keypad 56 can be used to decreased to commanded temperature (i.e., a lower steam temperature). The temperature hold command will now command the device to maintain the new commanded temperature. The temperature hold keypad 53 is a toggle, therefore, by depressing the temphold keypad a second time, deactivates the temperature hold function.

ASMS keypad 54 which when depressed activates the ASMS Hold Command which maintains a constant air-steam mixture (i.e., humidity) during operation, by command adjustments to heater 23a and fan motor 24 to maintain a constant air-steam mixture. Up scroll keypad 55 and the down scroll keypad 56 allow adjustments to be made to constant temperature and ASMS functions. The ASMS keypad 54 is also a toggle keypad function.

As best shown in FIG. 7 the device includes a Programmable Automatic Flow Adjusting Mechanism which is made up of the Flow Adjusting Mechanism as defined above, the electronics 28, and command software located within the CPU which is located inside the Hand-Held Remote Control 47. The Programmable Automatic Flow Adjusting Mechanism command software is assigned to the function keypad 49 under the functions "nozzle angle" and "nozzle speed". When the function keypad 49 is depressed, the menu of functions is called up and with repeative depression of the function keypad 49 cycles through the functions including the nozzle angle and nozzle speed functions.

The nozzle angle function programs the upper rotation limit and the lower rotation limit of the Programmable Automatic Flow Adjusting Mechanism. When the nozzle angle function prompts user to set upper limit, the up keypad 50 and down keypad 51 is used to scroll Part One 36 of Nozzle Section 1 to the desired upper limit. When the function keypad 49 is depressed again, the upper limit is set. The same procedure holds for setting the lower limit. Part 1 36 of Nozzle section 1 will then pivot within the upper and lower limits set by the nozzle angle function. For example, if upper limit is set at plus 45 degrees above Reference Line B and lower limit is set at minus 30 degrees below Reference Line B, Part One 36 of Nozzle section 1 will have a rotation angle of 75 degrees moving from plus 45 degrees relative to Reference Line B to minus 30 degrees relative to Reference Line B and vise-versa.

The nozzle speed function programs the speed at which Part One 36 of Nozzle Section 1 will travel while pivoting within the programmed limits set by the nozzle angle function. When the nozzle speed function is displayed on the LCD 46, Part One 36 of Nozzle section 1 begins to pivot within the preset limits. Adjustments to the speed are made by depressing the up keypad 50 to increase speed and the down keypad 51 to decrease speed.

The Programmable Flow Adjusting Mechanism is preset to have a stationary position and unless the nozzle angle function and nozzle speed function are re-programmed, via the function keypads 49 and the up keypad 50 and down keypad 51 then Part One 36 of Nozzle Section 1 will remain stationary. The Programmable Automatic Flow Adjusting Mechanism has a software feature which allows Part One 36 of Nozzle Section 1 to be motor 34 driven to a new fixed position via the up keypad 50 and down keypad 51.

The safety lock that requires a key (not shown) in order to operate the steaming device. This feature guards the device against accidental operation and/or mishandling by children and other not experienced in the operation of this type of device.

USE AND OPERATION

In order to use the steaming device of the present invention, the user gains access to left chamber 22 via the rear access panel 27. The user then removes the reservoir 23b and fills it to a desired volume. After placing reservoir back into left chamber and securing rear access panel 27, the user positions the upper external support structure 2 to a desired position within the optimized treatment zone and then secures the structure with the spring loaded locking rod (not shown). The user will then level the nozzle section 1 by loosening butterfly screw 19 and then rotate the entire nozzle section 1 until level. The user will then secure the nozzle section 1 by tightening the butterfly screw 19. If desired, the user can then reconfigure Part One 36 of Nozzle section 1, to tailor the steaming device to his or her need (i.e., changing Reference Line B). The electric cable (not shown) of the device is then connected to a power source. The user then releases the safety lock (not shown). The user then powers up the device by depressing Power keypad 48 located on the Hand-Held Remote Control 47. Desired selections of time, temperature, fan speed, air-steam optimization, angle and speed of the automatic flow adjusting mechanism, etc., are made by setting control functions on the hand-held remote control 47. After a certain time has elapsed, the water in reservoir 23 begins to turn into steam, which is mixed with the ambient air drawn into reservoir 23 via suction motor 24 and driving fan 25. The air-steam mixture then flows upwardly through conduit 5 and enters nozzle section 1 and exhausted into the atmosphere through converging nozzles I, II, and III. It should be noted that due to the constant flow of ambient air drawn into reservoir 23, and continuous production of steam therein, a fluid pressure is developed in reservoir 23, which propels the airsteam upwardly through conduit 5.

If the Programmable Automatic Flow Adjusting Mechanism has not been actuated, the Part One 36 of Nozzle section 1 will not move, and the air stream would be blown straight out and would only affect the area of skin lying directing in front of it. However if the user wishes to obtain a sweeping action of the air steam, the Programmable Automatic Flow Adjusting Mechanism can be easily actuated via the hand held remote control 47 to cause the Part One 36 to move in a sweeping action. The speed at which Part One 36 sweeps is also controlled via the hand-held remote control 47. This unique arrangement offers the flexibility of treating a relatively larger skin area.

As can be seen from the above, the device of the present invention is versatile, simple to use, and can be easily assembled and disassembled for use or compact shipment.

While this invention has been described as having a preferred design, it is understood that it is capable of further modifications, uses, and/or adaptations of the invention following in general the principal of the invention and including such departures from the present disclosure as come within known or customary practice in the art to which the invention pertains, and as may be applied to the central features hereinbefore set forth and fall with the scope of the invention of the limits of the claims appended hereto.

What I claim is:
1. A steaming device, comprising:
   a) a reservoir for containing therein a predetermined quantity of water;
   b) a heater in operative engagement with said reservoir for heating the water and thereby producing steam;
   c) a nozzle for exhausting out the steam;
   d) a conduit for connecting said nozzle with said reservoir;
   e) said nozzle including an automatic flow adjusting means for selectively varying the direction of the steam flowing out therefrom;
   f) said automatic flow adjusting means including a programmable computerized control system;
   g) a support structure for supporting components of said device;
   h) said nozzle includes an opening communicating with an no exterior.
2. The device of claim 1, and including:
   a) means for introducing ambient air in said reservoir for mixing with and pushing steam.
3. The device of claim 2, wherein:
   a) said means for introducing ambient air comprising a suction motor.
4. The device of claim 1, wherein:
   a) said support structure includes a structure which independently supports said components of said device.
5. The device of claim 1, wherein:
   a) said support structure includes a rigid external shell which encloses said components and independently supports said components of said device.
6. The device of claim 1, and including:
   a) means for allowing the height of said nozzle to be altered.
7. The device of claim 1, including:
   a) said support structure includes an upper support structure and lower support structure.
8. The device of claim 7, including:
   a) means for allowing said upper support structure to pivot about a horizontal axis.
9. The device of claim 7, including:
   a) means for allowing said nozzle to pivot relative to said upper support structure.
10. The device of claim 1, wherein:
    a) said automatic flow adjusting means comprises a generally pivotal mounted nozzle.
11. The device of claim 1, wherein:
    a) said automatic flow adjusting means comprises a first sprocket and a second sprocket mounted to said nozzle and a motor, respectively.
12. The device of claim 11, wherein:
    a) said first sprocket and said second sprocket are interconnected and rotate together as one integral unit, such that when said second sprocket rotates, said nozzle rotates.
13. The device of claim 12, wherein:
    a) said programmable computerized control system comprises a nozzle control for selectively rotating said nozzle.
14. The device of claim 13, wherein:
    a) said nozzle control includes means for selecting rotational limits between which said nozzle will rotate.
15. The device of claim 13, wherein:
    a) said nozzle control includes means for selecting the speed at which said nozzle will rotate.
16. The device of claim 1, wherein:
    a) said nozzle includes at least one internally mounted converging nozzle.
17. The device of claim 1, wherein:
    a) said nozzle includes internally mounted redirection channels for reducing induced turbulence by controlling turn rate of steam.
18. The device of claim 1, including:
    a) control means for maintaining constant steam temperature or constant humidity during operation of said device.

* * * * *